(12) United States Patent
Mägerlein et al.

(10) Patent No.: US 8,710,269 B2
(45) Date of Patent: Apr. 29, 2014

(54) DMAPN HAVING A LOW DGN CONTENT AND A PROCESS FOR PREPARING DMAPA HAVING A LOW DGN CONTENT

(75) Inventors: Wolfgang Mägerlein, Mannheim (DE); Jan Eberhardt, Mannheim (DE); Johann-Peter Melder, Böhl-Iggelheim (DE); Ulrich Köhler, Mannheim (DE); Thilo Hahn, Kirchheimbolanden (DE); Mirko Kreitschmann, Mannheim (DE); Dominik Herbrecht, Heidelberg (DE)

(73) Assignee: BASF SE, Ludwigshafen (DE)

( * ) Notice: Subject to any disclaimer, the term of this patent is extended or adjusted under 35 U.S.C. 154(b) by 19 days.

(21) Appl. No.: 13/191,963

(22) Filed: Jul. 27, 2011

(65) Prior Publication Data

US 2012/0029225 A1 Feb. 2, 2012

Related U.S. Application Data

(60) Provisional application No. 61/368,656, filed on Jul. 29, 2010.

(51) Int. Cl.
| | | |
|---|---|---|
| *C07C 209/48* | (2006.01) | |
| *C07C 211/11* | (2006.01) | |
| *C07C 255/24* | (2006.01) | |
| *C07C 255/25* | (2006.01) | |

(52) U.S. Cl.
CPC ............. *C07C 209/48* (2013.01); *C07C 211/11* (2013.01); *C07C 255/24* (2013.01); *C07C 255/25* (2013.01)
USPC .......................................... 564/490; 558/452

(58) Field of Classification Search
CPC ............................ C07C 209/48; C07C 211/11
USPC .......................................... 564/490; 558/452
See application file for complete search history.

(56) References Cited

U.S. PATENT DOCUMENTS

| | | | |
|---|---|---|---|
| 4,172,091 A | 10/1979 | Weber et al. | |
| 5,536,691 A | 7/1996 | Breitscheidel et al. | |
| 5,696,048 A | 12/1997 | Breitscheidel et al. | |
| 6,790,996 B2 | 9/2004 | Ansmann et al. | |
| 7,723,547 B2 * | 5/2010 | Ernst et al. | 564/490 |
| 2008/0293973 A1 | 11/2008 | Ernst et al. | |
| 2009/0069590 A1 | 3/2009 | Eberhardt et al. | |
| 2011/0137029 A1 | 6/2011 | Kubanek et al. | |
| 2011/0137030 A1 | 6/2011 | Kubanek et al. | |
| 2011/0172430 A1 | 7/2011 | Ernst et al. | |

FOREIGN PATENT DOCUMENTS

| | | | |
|---|---|---|---|
| DE | 222011 A1 | 5/1985 | |
| EP | 636409 A1 | 2/1995 | |
| EP | 742045 A1 | 11/1996 | |
| EP | 1306365 A2 | 5/2003 | |
| WO | WO-2007051786 A1 | 5/2007 | |
| WO | WO 2007051786 A1 * | 5/2007 | |
| WO | WO-2007/128803 A1 | 11/2007 | |
| WO | WO 2007128803 A1 * | 11/2007 | |
| WO | WO-2010/089265 A2 | 8/2010 | |
| WO | WO-2010/106133 A1 | 9/2010 | |
| WO | WO-2010/133630 A2 | 11/2010 | |
| WO | WO-2011/082967 A1 | 7/2011 | |
| WO | WO-2011/082994 A1 | 7/2011 | |

OTHER PUBLICATIONS

International Search Report of PCT/EP2011/062496 dated Dec. 14, 2011.
U.S. Appl. No. 13/080,080, filed Oct. 13, 2011, Melder, Johann-Peter.
U.S. Appl. No. 13/080,885, filed Mar. 13, 2014, Melder, Johann-Peter.
U.S. Appl. No. 13/116,649, filed Dec. 1, 2011, Melder, Johann-Peter.
U.S. Appl. No. 13/039,109, filed Mar. 2, 2011, Suter et al.
U.S. Appl. No. 13/127,828, filed May 5, 2011, Wigbers et al.
U.S. Appl. No. 13/128,508, filed May 10, 2011, Dahmen et al.
U.S. Appl. No. 13/112,161, filed May 20, 2011, Chedid et al.
U.S. Appl. No. 13/158,667, filed Jun. 13, 2011, Wigbers et al.
U.S. Appl. No. 13/141,016, filed Jun. 20, 2011, Melder et al.
U.S. Appl. No. 13/173,437, filed Jun. 30, 2011, Huyghe et al.
U.S. Appl. No. 13/148,595, filed Aug. 9, 2011, Wigbers et al.

* cited by examiner

*Primary Examiner* — Yong Chu
(74) *Attorney, Agent, or Firm* — Novak Druce Connolly Bove + Quigg LLP

(57) ABSTRACT

The present invention relates to a process for preparing 3-dimethylaminopropylamine (DMAPA) by reacting 3-dimethylaminopropionitrile (DMAPN) with hydrogen in the presence of a catalyst, wherein the DMAPN used has a content of 2-(dimethylaminomethyl)glutaronitrile (DGN) of 300 ppm by weight or less, based on the DMAPN used.

Furthermore, the present invention relates to mixtures of DMAPN and DGN, wherein the weight ratio of DMAPN to DGN is in the range from 1 000 000:5 to 1 000 000:250.

18 Claims, No Drawings

DMAPN HAVING A LOW DGN CONTENT AND A PROCESS FOR PREPARING DMAPA HAVING A LOW DGN CONTENT

CROSS-REFERENCE TO RELATED APPLICATIONS

The provisional application (U.S. 61/368,656) filed on Jul. 29, 2010 is incorporated by reference into the present application.

BACKGROUND OF THE INVENTION

The present invention relates to a process for preparing 3-dimethylaminopropylamine (DMAPA). The present invention further relates to mixtures of DMAPN and 2-(dimethylaminomethyl)-glutaronitrile (DGN) having a low DGN content.

3-Dimethylaminopropylamine (DMAPA, N,N-dimethyl-1,3-diaminopropane) is an important intermediate for industrial production of, for example, liquid soaps. DMAPA also serves as starting material for the preparation of coagulants and should itself have anticorrosive properties.

DMAPA is generally prepared by means of a two-stage process.

In the first stage, acrylonitrile (ACN) is usually reacted with dimethylamine (DMA), generally forming 3-dimethylaminopropionitrile (DMAPN).

DMAPN is then generally reduced to DMAPA in a further stage.

According to WO 2007/128803, it is advantageous to use an integrated production process or an integrated apparatus for preparing DMAPA. Here, the product stream initially obtained, which comprises DMAPN, is used directly or after purification for conversion into DMAPA in a further step. According to the teaching of WO 2007/128803, the quality of the DMAPN product stream from the first reaction (DMA and ACN) is of critical importance for the reduction reaction of DMAPN to DMAPA, in particular in respect of the consumption of the catalyst used in the reduction.

WO 2007/128803 therefore teaches a process for preparing DMAPN by continuous reaction of DMA with ACN, with firstly DMA and subsequently ACN being introduced continuously and the reaction of the reaction stream occurring in a first reaction region and at least partly in a second reaction region.

The DMAPN obtained in this way is then, generally without further work-up, reduced directly by means of hydrogen to DMAPA in a further reaction region.

According to the disclosure, the operating life of the hydrogenation catalyst in the hydrogenation of DMAPN can be increased when a DMAPN prepared according to the teaching of WO 2007/128803 in two separate reaction spaces is used in the hydrogenation of DMAPN.

BRIEF SUMMARY OF THE INVENTION

The object of the present invention compared to the prior art was to achieve a further improvement in the operating life of the catalysts used in the hydrogenation of DMAPN. In particular, undesirable secondary reactions such as exothermic decomposition of the nitrile, redissociation of DMAPN into ACN and DMA or formation of secondary amines by condensation of DMAPA should be kept low during the use of the catalyst, without the space velocity over the catalyst having to be reduced. From an industrial point of view, a low content of DMAPN in the product is advantageous since DMAPN is difficult to separate from DMAPA and in subsequent uses leads to undesirable properties such as odor and discoloration. Although the content of DMAPN in the hydrogenation output can be decreased to a certain extent by increasing the reaction temperature above the initial value since this leads to a higher conversion, the increase in the reaction temperature results in formation of other secondary components which reduce the quality. For this reason, the reaction temperature cannot be increased at will. It was accordingly an object of the present invention to keep deactivation of the catalyst low during the process in order to increase the life of the catalyst while maintaining good performance of the catalyst. A measure of these properties is the ratio of temperature increase to time of operation. A low ratio of temperature increase to time of operation means that the catalyst can be operated for a long time at the initial temperature and that the temperature increase required to compensate for any catalyst deactivation is small. Critical temperatures at which the secondary reactions increase to an excessive extent are thus not reached for a long time. It was therefore also an object of the present invention to minimize the ratio of temperature increase to time of operation of the catalyst.

The object of the present invention was able to be achieved by a process for preparing 3-dimethylaminopropylamine (DMAPA) by reacting 3-dimethylaminopropionitrile (DMAPN) with hydrogen in the presence of a catalyst, wherein the DMAPN used has a content of 2-(dimethylaminomethyl)glutaronitrile (DGN) of 300 ppm by weight or less, based on the DMAPN used.

DETAILED DESCRIPTION OF THE INVENTION

It has surprisingly been found that 2-(dimethylaminomethyl)glutaronitrile (DGN) of the formula (I)

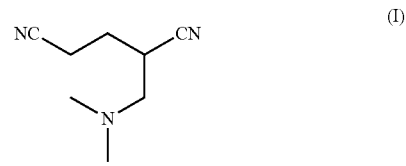

in the DMAPN leads to more rapid deactivation of nitrile hydrogenation catalysts. On the other hand, when the DGN content does not exceed a value of 300 ppm, a further increase in the operating life compared to the prior art can be achieved. Although WO 2007/128803 discloses that the quality of the DMAPN used in the hydrogenation can be critical to the quality of the DMAPA obtained by hydrogenation of DMAPN, it gives no information about which properties of the DMAPN influence the hydrogenation reaction. Furthermore, a DMAPN having a DGN content of 300 ppm and less is not disclosed directly and unambiguously in the context of the process disclosed in WO 2007/128803. In addition, other documents of the prior art (e.g. WO-A-2007/051786, DD-A-58306, DD-A-222011, U.S. Pat. No. 4,172,091) give neither unambiguous and direct information as to how a DMAPN having a DGN content of 300 ppm can be prepared nor that the DGN content of the DMAPN affects the subsequent hydrogenation.

In the process of the invention, a DMAPN having a content of 300 ppm or less of DGN, based on the DMAPN used, is used. Preference is given to using a DMAPN having a DGN content of 250 ppm or less, particularly preferably 150 ppm or less and particularly preferably 50 ppm or less, in the process of the invention.

In a preferred embodiment, DMAPN having a content of 300 ppm or less of DGN can be prepared by continuous reaction of ACN with DMA and subsequent distillation. In this preferred embodiment, the preparation of DMAPN can in principle be carried out in a manner analogous to the teaching of WO 2007/128803 or the teaching of WO 2007/051786, whose contents are expressly incorporated by reference.

In this preferred embodiment, the reaction of ACN with DMA is preferably carried out in a reactor cascade in which preferably from 2 to 10, particularly preferably from 2 to 8 and very particularly preferably from 3 to 7 reactors are connected in series. The reaction of DMA with ACN in a reactor cascade makes it possible to set different reaction conditions. In this way, more complete reaction of ACN combined with minimization of the proportion of by-products in the reaction stream can be achieved.

The reactors of the reactor cascade can be, for example, stirred tank reactors, reactors having an external pump circuit (loop reactors) or tube reactors with preference being given to the first reactor or first reactors of the reactor cascade being stirred tank reactors and the last reactor or last reactors of the reactor cascade being tube reactors.

In the preferred embodiment, the reaction temperature in the reactors is preferably in the range from 20° C. to 120° C. The range is more preferably from 40° C. to 90° C., with further preference being given to the temperature in the last reactor or last reactors of the reactor cascade being lower than the reaction temperature in the first reactor or first reactors of the reactor cascade. In the preferred embodiment, the reaction of ACN and DMA is preferably carried out in a pressure range from 1 bar to 20 bar, preferably from 2 to 15 bar and particularly preferably from 3 to 8 bar, with the pressure generally being determined by the autogenous pressure of the DMA used under the respective reaction conditions.

In a very particularly preferred embodiment, the reaction of ACN with DMA is carried out in the presence of water.

When the reaction is carried out in the presence of water, preference is given to the proportion of water, based on the sum of the ACN and DMA used, being in the range from 0.5 to 10% by weight, particularly preferably in the range from 1 to 8% by weight and very particularly preferably in the range from 3 to 7% by weight. The molar ratio of DMA to ACN is then preferably from 1.00:1 to 1.10:1, preferably from 1.01:1 to 1.08:1 and particularly preferably from 1.02:1 to 1.06:1.

If no additional water is used in the reaction, it is advantageous to use a molar excess of DMA. The molar ratio of DMA to ACN is then preferably greater than 1.02:1, particularly preferably from 1.04:1 to 1.35:1 and very particularly preferably from 1.06:1 to 1.25:1.

In the preferred embodiment, ACN and DMA and optionally water can be fed in together or separately. DMA and ACN are preferably fed in separately. They are particularly preferably fed in by firstly introducing DMA into a circulation stream which already comprises DMAPN and preferably introducing ACN after DMA and DMAPN have been combined.

The water can, for example, be introduced in the form of an additional feed stream into the reaction stream. Furthermore, it is possible for at least part of the DMA to be introduced in the form of an aqueous solution into the reaction stream. For example, this can be in the form of a 30-70% strength by weight aqueous DMA solution. In addition, the ACN used can comprise water.

Furthermore, it has been found to be advantageous for DMA and ACN to be introduced in liquid form. This allows a higher conversion at a better space-time yield compared to processes in which DMA is introduced in gaseous form into the reaction mixture. The ACN and DMA introduced therefore have a suitable temperature and a suitable pressure which ensure that these starting materials for preparing DMAPN are present in liquid form.

In the preferred embodiment, the continuous reaction of ACN with DMA gives a DMAPN-comprising reaction mixture as reaction output which can comprise not only DMAPN but generally also unreacted DMA, DGN and further organic compounds and also possibly water and possibly unreacted ACN.

Part of the DMAPN can be recirculated as recycle stream or circulation stream to the process, in which case it is preferably recirculated to a point downstream of the first reactor.

The DMAPN reaction mixture obtained in this preferred embodiment is subsequently introduced into a thermal separation sequence in which both volatile and high-boiling secondary components are separated off from DMAPN.

This can preferably be carried out using a column arrangement comprising a column for separating off low boilers and a further distillation column for separating off the relatively nonvolatile secondary components.

The removal of the low and high boilers can particularly preferably be carried out in a column in which low boilers are obtained at the top, high boilers are obtained at the bottom and DMAPN is obtained via a gaseous side offtake stream.

In a further particularly preferred embodiment, the removal of the low and high boilers can be carried out in a column which has a dividing wall in the middle part and in which the low boilers are obtained at the top, high boilers are obtained at the bottom and DMAPN is obtained at the side of the dividing wall opposite the feed point.

Low boilers (LB) such as DMA, ACN, possibly water and other low-boiling secondary components are obtained at the top of the low boiler column or of the enrichment section. High boilers (HB) relative to DMAPN are DGN and possibly other secondary components having a low vapor pressure. These are separated off via the bottoms from the stripping section or the stripping column.

The precise operating conditions of the distillation sequence can be determined by a person skilled in the art on the basis of the separation performance of the column internals used and measured or estimated vapor pressures and vapor-liquid equilibria (VLE) of the components introduced into the distillation sequence using conventional calculation methods.

The distillation sequence preferably has internals for increasing the separation performance. The distillation internals can be, for example, in the form of trays, beds of packing elements or ordered packing. In the case of a dividing wall column, preference is given to using ordered packings. An advantage of the use of ordered packings is the low pressure drop and the low specific liquid holdup compared to trays such as valve trays. The internals can be present in one or more beds.

The reaction output from the preparation of DMAPN is preferably fed to a three-dimensional region having from 25% to 75% of the theoretical plates of the distillation column (counted from the bottom). For example, the introduction can be effected somewhat below the middle of the theoretical plates. The optimum feed point can be determined by a person skilled in the art using conventional calculation tools.

The number of theoretical plates for separating off the low boilers, known as the enrichment section, is generally in the range from 10 to 50, preferably from 10 to 30. The number of theoretical plates for separating off the high boilers, known as the stripping section, is generally in the range from 10 to 50, preferably from 10 to 30.

The pressure at the top of the distillation column(s) is particularly preferably from 0.1 to 10 bar, particularly preferably from 0.5 to 5 bar. The distillation column(s) is/are very particularly preferably operated at atmospheric pressure.

If the removal of the low and high boilers is carried out in a column arrangement comprising a column for separating off low boilers and a further distillation column for separating off the relatively nonvolatile secondary components, a temperature which is above the boiling point of water but below the boiling point of DMAPN is preferably set at the bottom of the low boiler column. For example, a temperature at the bottom of the column of from 100 to 170° C., particularly preferably from 110 to 150° C., can preferably be set at a pressure at the top of 1 bar (abs.). At the bottom of the high boiler column, a temperature which is above the boiling point of DMAPN but below the boiling point of DGN is preferably set. For example, a temperature at the bottom of the column of from 170 to 200° C., particularly preferably from 180 to 195° C., can preferably be set in the stripping column at a pressure at the top of the column of 1 bar (abs.). The condenser of the low boiler column is generally operated at a temperature at which the major part of the DMA and water is condensed at the respective pressure at the top. In general, the operating temperature of the condenser is in the range from 25 to 100° C., preferably from 25 to 50° C.

Preference is given to recirculating more than 30% by weight, preferably more than 50%, by weight of the condensate obtained at the condenser to the top of the low boiler column. The energy required for vaporization is usually introduced by means of an internal or external vaporizer at the bottom of the column.

A condensate which comprises predominantly DMA and possibly water and possibly other low-boiling organic secondary components is obtained in the condenser of the low boiler column. This condensate can be recirculated as starting material to the reaction for the synthesis of DMAPN.

In the bottoms from the low boiler column, DMAPN is obtained as bottom product together with DGN and possibly other relatively nonvolatile secondary components.

In the bottoms from the stripping column, DGN is obtained as bottom product together with any other relatively nonvolatile secondary components (DGN removal).

DMAPN is obtained at the top of the stripping column.

If the low and high boilers are separated off in a distillation column in which low boilers are obtained at the top, high boilers are obtained at the bottom and DMAPN is obtained via a liquid or gaseous side offtake stream or in a column which has a dividing wall in the middle part and in which the low boilers are obtained at the top, high boilers are obtained at the bottom and DMAPN is obtained at the side of the dividing wall opposite the feed point, preference is given to setting a temperature at the bottom of the column which is above the boiling point of DMAPN but below the boiling point of DGN. For example, a temperature at the bottom of the column of from 170 to 200° C., particularly preferably from 180 to 195° C., can preferably be set at a pressure at the top of the column of 1 bar (abs.).

The condenser of the distillation column is generally operated at a temperature at which the major part of the DMA and water is condensed at the respective pressure at the top. In general, the operating temperature of the condenser is in the range from 25 to 100° C., preferably from 25 to 50° C.

Preference is given to recirculating more than 30% by weight, preferably more than 50% by weight, of the condensate obtained at the condenser to the top of the distillation column. The energy required for vaporization is usually introduced by means of an internal or external vaporizer in the bottom of the column.

A condensate comprising predominantly DMA and possibly water and possibly other low-boiling organic secondary components is obtained in the condenser.

This condensate can be recirculated as starting material to the reaction for the synthesis of DMAPN.

In the bottoms from the stripping section, DGN is obtained as bottom product together with any other relatively nonvolatile secondary components (DGN removal).

DMAPN is obtained via a liquid or gaseous side offtake stream or at the side of the dividing wall opposite the feed point.

The DMAPN obtained as product of the separation sequence usually has a content of more than 95% by weight of DMAPN, preferably more than 98% by weight of DMAPN and particularly preferably more than 99% by weight of DMAPN.

The DMAPN obtained in this preferred embodiment preferably has a DGN content of 300 ppm or less based on DMAPN, particularly preferably a content of 250 ppm or less based on DMAPN, very particularly preferably a content of 150 ppm or less based on DMAPN and in particular a content of 50 ppm or less based on DMAPN.

In a very particularly preferred embodiment, the reaction of dimethylamine and acrylonitrile is carried out in the presence of water in a reactor cascade in a temperature range from 50 to 80° C. and a pressure range from 3 to 8 bar, with the molar ratio of DMA to ACN being in the range from 1.02:1 to 1.10:1 and the proportion of water being in the range from 1 to 8% by weight, based on the sum of the ACN and DMA used. If these reaction conditions are adhered to, a work-up by distillation of the reaction output from the preparation of DMAPN is generally not necessary in order to obtain a DMAPN having a DGN content of 300 ppm or less.

The weight ratio of DMAPN to DGN in the DMAPN obtained in this way is preferably in the range from 1 000 000:1 to 1 000 000:300, particularly preferably in the range from 1 000 000:5 to 1 000 000:250, very particularly preferably in the range from 1 000 000:8 to 1 000 000:150 and in particular in the range from 1 000 000:10 to 1 000 000:100.

The present invention accordingly also provides a mixture of DMAPN and DGN, wherein the weight ratio of DMAPN to DGN is in the range from 1 000 000:5 to 1 000 000:250.

The DGN content of the DMAPN can easily be determined by the analytical methods known to those skilled in the art, for example by gas chromatography.

Furthermore, hydrogen is used in the process of the invention for preparing DMAPA. As reducing agent, it is possible to use hydrogen or a hydrogen-comprising gas. The hydrogen is generally used in industrial purity. The hydrogen can also be used in the form of a hydrogen-comprising gas, i.e. in admixture with other inert gases such as nitrogen, helium, neon, argon or carbon dioxide. As hydrogen-comprising gases, it is possible to use, for example, reformer offgases, refinery gases, etc., if and insofar as these gases do not comprise any catalyst poisons for the hydrogenation catalysts used, for example CO. However, preference is given to using pure hydrogen or essentially pure hydrogen in the process, for example hydrogen having a content of more than 99% by weight of hydrogen, preferably more than 99.9% by weight of hydrogen, particularly preferably more than 99.99% by weight of hydrogen, in particular more than 99.999% by weight of hydrogen.

The reaction of DMAPN having a DGN content of 300 ppm or less and hydrogen can be carried out in the presence of ammonia. Preference is given to using pure ammonia in the process, preferably ammonia having a content of more than 99% by weight of ammonia and particularly preferably more than 99.9% by weight of ammonia.

In a preferred embodiment, ammonia is generally used in molar ratios to the nitrile group of from 0.5:1 to 100:1, preferably from 2:1 to 20:1.

A further preferred embodiment is a process in which no ammonia is added.

The reaction of DMAPN having a DGN content of 300 ppm or less with hydrogen is carried out in the presence of a catalyst.

As catalysts for the hydrogenation of the nitrile function to form the amine, it is possible to use, in particular, catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species. These include skeletal catalysts (also referred as Raney® type, hereinafter also: Raney catalyst) which are obtained by leaching (activating) an alloy of hydrogenation-active metal and a further component (preferably Al). The catalysts can additionally comprise one or more promoters. In a particularly preferred embodiment, Raney nickel catalysts or Raney cobalt catalysts are used.

The catalysts can be used as all-active catalysts or in supported form. As supports, preference is given to using metal oxides such as $Al_2O_3$, $SiO_2$, $ZrO_2$, $TiO_2$, mixtures of metal oxides or carbon (activated carbons, carbon black, graphite).

The oxidic catalysts are activated outside the reactor or in the reactor by reduction of the metal oxides in a hydrogen-comprising gas stream at elevated temperature before use. When the catalysts are reduced outside the reactor, this can be followed by passivation by means of an oxygen-comprising gas stream or embedding in an inert material in order to avoid uncontrolled oxidation in air and allow safe handling. Before the passivated catalysts are used in the reaction, they are usually reactivated by means of a hydrogen-comprising gas at elevated temperature.

Particularly preferred fixed-bed catalysts are the all-active cobalt catalysts disclosed in EP-A-0 742 045 or EP-A-0 636 409, doped with Mn, P and alkali metal (Li, Na, K, Rb, Cs). The catalytically active composition of these catalysts before reduction with hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A-1306365, which comprise cobalt and if appropriate additionally nickel and also at least one further doping metal on a particulate support material, wherein the cobalt and optionally the nickel have an average particle size of from 3 to 30 nm in the active catalyst.

The process of the invention for preparing DMAPA is preferably carried out continuously. This allows a particularly efficient conversion combined with a high space-time yield. However, the preparation of DMAPA can also be carried out batchwise or semicontinuously.

Typical reactors in which the hydrogenation can be carried out are, for example, high-pressure stirred tank reactors, loop reactors, autoclaves or fixed-bed reactors.

The process of the invention is preferably carried out in a high-pressure stirred tank reactor or fixed-bed reactor. Very particular preference is given to carrying out the hydrogenation in a fixed-bed reactor.

The reaction mixture can flow through the fixed-bed reactor from the top downward (downflow mode) or from the bottom upward (upflow mode).

Hydrogen, DMAPN and optionally ammonia can be introduced together, for example as premixed reactant stream, or separately into the reaction zone of the reactor.

Furthermore, a recycle stream or circulation stream can be introduced.

The hydrogenation is generally carried out at a pressure of from 1 to 500 bar, preferably from 10 to 400 bar, particularly preferably at a pressure of from 20 to 300 bar and very particularly preferably from 30 to 200 bar. Maintenance or control of the pressure is generally affected via the introduction of the hydrogen.

The hydrogenation is generally carried out at temperatures of from 20 to 400° C., preferably from 40 to 250° C., particularly preferably from 50 to 180° C. and very particularly preferably from 70 to 150° C.

The reaction output from the hydrogenation reactor is preferably passed through a heat exchanger. After passage through the heat exchanger, the temperature of the hydrogenation output is preferably in the range from 20 to 80° C.

In a preferred embodiment, the hydrogenation is carried out adiabatically.

The hydrogenation output is usually worked up after the hydrogenation. In general, hydrogen and ammonia are separated from the hydrogenation output and after the separation can be recirculated to the process.

To work up the hydrogenation output, the latter is preferably introduced into a separator in which liquid crude product is separated off from gaseous components such as hydrogen, DMA and ammonia and can be discharged via an outlet.

In a preferred embodiment, the crude product can be at least partly recirculated to the reaction stream in a recycle mode.

The mixture of hydrogen, DMA and ammonia obtained can be discharged from the phase separator via a further outlet and can likewise preferably be recirculated to the process or, optionally after separation, to the preparation of DMAPN.

The present invention makes it possible to achieve a further improvement in the operating life of the catalysts used in the hydrogenation of DMAPN compared to the prior art.

In particular, undesirable secondary reactions such as the exothermic decomposition of the nitrile, the redissociation of DMAPN into ACN and DMA or the formation of secondary amines by condensation of DMAPA during the use of the catalyst can be kept low without the space velocity over the catalyst having to be reduced. From an industrial point of view, a low content of DMAPN in the product is advantageous since DMAPN is difficult to separate from DMAPA and in subsequent uses leads to undesirable properties such as odor and discoloration. Although the content of DMAPN in the hydrogenation output can to a certain extent be compensated for by increasing the reaction temperature to above the initial value since this leads to a higher conversion, the increase in the reaction temperature results in formation of other secondary components which reduce the quality, so that the reaction temperature cannot be increased at will. The process of the invention makes it possible to keep deactivation of the catalyst low during the process in order to increase the life of the catalyst at a constant good performance of the catalyst. A measure of these properties is the ratio of temperature increase to operating time. A low ratio of temperature increase to operating time means that the catalyst can be operated for a long time at the initial temperature and that the temperature increase required to compensate for any catalyst deactivation is small, so that a critical temperature at which the secondary reactions increase excessively is not reached for a long time. The process of the invention enables the ratio of temperature increase to operating time of the catalyst to be reduced.

The present invention is illustrated by the following examples.

EXAMPLES

Examples A to C

Preparation of 3-dimethylaminopropionitrile (DMAPN) as Starting Material for Examples 1-3

General Procedure:
DMAPN was prepared by reaction of acrylonitrile (ACN) and dimethylamine (DMA), optionally in the presence of small amounts of water.

A continuous apparatus comprising a cascade of three stirring autoclaves (C1 to C3) connected in series was used. C1 had a volume of 80 ml, C2 had a volume of 120 ml and C3 had a volume of 200 ml. Four further stirring autoclaves could optionally be connected in series after C3: C4, C5, C6 and C7 each having a volume of 270 ml. For the present purposes, the volume is the volume filled with liquid.

ACN, DMA and optionally water were introduced simultaneously into the plant upstream of C1. The plant was operated in a single pass. The pressure in the autoclaves was 5 bar.

The DMAPN prepared in this way was fed without further work-up directly into the hydrogenation stage (Examples 1 to 3). Part of the crude DMAPN was separated off and analyzed for secondary components.

Example A

Preparation of DMAPN for Example 1

Use of C1, C2 and C3
Temperature in C1: 60° C.; temperature in C2: 70° C.; temperature in C3: 70° C.
Feed rate of ACN: 43.3 g/h
Feed rate of DMA: 37.5 g/h (excess of 2 mol % of DMA over ACN)
Feed rate of water: 2.1 g/h (corresponds to 2.6% by weight based on the amount of DMA and ACN used)
Analysis for secondary components:
To analyze the high-boiling secondary products, an amount of 1403 g of the DMAPN prepared in this way was concentrated to a residue of 10-15 g in a distillation apparatus having a Vigreux column at 100 mbar and a temperature at the top of 100-105° C. up to a maximum temperature at the bottom of 135° C.
A GC analysis was carried out on this residue:
GC column: 30 m RTX-5; ID=0.32 mm, film thickness=1.5 μm
Temperature program: 70° C.-7° C./min-280° C.-30 min
DGN was detected at a retention time of 16 min.
The content of DGN, based on the amount of DMAPN originally used in the distillation (1403 g), was 227 ppm.

Example B

Preparation of DMAPN for Example 2

Use of C1, C2, C3, C4, C5, C6 and C7
Temperature in C1: 60° C.; temperature in C2: 70° C.; temperature in C3: 70° C.; temperature in C4: 70° C.; temperature in C5: 70° C.; temperature in C6: 70° C.; temperature in C7: 60° C.
Feed rate of ACN: 43.3 g/h
Feed rate of DMA: 37.5 g/h (excess of 2 mol % of DMA over ACN)
Analysis for secondary components:
To analyze the high-boiling secondary products, an amount of 1406 g of the DMAPN prepared in this way was concentrated to a residue of 10 g in a distillation apparatus having a Vigreux column at 100 mbar and a temperature at the top of 100-105° C. up to a maximum temperature at the bottom of 135° C.
A GC analysis was carried out on this residue (cf. Example a)):
The content of DGN, based on the amount of DMAPN originally used in the distillation (1406 g), was 373 ppm.

Example C

Preparation of DMAPN for Example 3

Use of C1, C2, C3, C4, C5, C6 and C7
Temperature in C1: 60° C.; temperature in C2: 70° C.; temperature in C3: 70° C.; temperature in C4: 70° C.; temperature in C5: 70° C.; temperature in C6: 70° C.; temperature in C7: 60° C.
Feed rate of ACN: 43.3 g/h
Feed rate of DMA: 37.5 g/h (excess of 2 mol % of DMA over ACN)
Feed rate of water: 4 g/h
To analyze the high-boiling secondary products, an amount of 1014 g of the DMAPN prepared in this way was concentrated to a residue of 5.3 g in a distillation apparatus having a Vigreux column at 100 mbar and a temperature at the top of 100-105° C. up to a maximum temperature at the bottom of 135° C.
A GC analysis was carried out on this residue (cf. Example a)):
The content of DGN, based on the amount of DMAPN originally used in the distillation (1014 g), was 27 ppm.

Examples 1 to 3

Hydrogenation of the DMAPN from Examples A to C

General Procedure:
The continuous hydrogenation of DMAPN to DMAPA was carried out in a vertical tube reactor having a heatable length of 100 cm and an internal diameter of 6 mm (reactor volume: about 28 ml).

The reactor was charged with 26 g of a cobalt catalyst produced as described in EP-A-0636409 (illustrative catalyst A).

A solution comprising 10% by weight of cobalt, 0.55% by weight of manganese and 0.45% by weight of $H_3PO_4$ was produced by dissolving cobalt nitrate, manganese nitrate and phosphoric acid in water. Precipitation was carried out at a temperature of 50° C. by addition of a 20% strength sodium carbonate solution. The precipitate formed was washed until no sodium or nitrate could be detected in the washing water. The solid obtained in this way was slurried with water and sprayed in a spray dryer (inlet temperature=550° C.). The spray-dried material was dried at 500° C., processed in a pan mill and shaped in an extruder to give extrudates having a diameter of 4 mm. The extrudates were dried at 100-120° C. and subsequently calcined at 650° C. for 1 hour and then 850° C. for 3 hours.

The catalyst precursor produced in this way comprised 90.4% by weight of cobalt, 5.1% by weight of manganese, 0.3% by weight of sodium and 3.1% by weight of phosphorus.

The catalyst was subsequently reduced ($H_2$, 300° C., 1 bar) and passivated ($N_2/O_2$; 50° C., 1 bar). In this state, the shaped catalyst bodies were installed in the tube reactor and the laboratory plant was made inert by means of nitrogen.

The catalyst was heated to 280° C. over a period of 12 hours under a stream of hydrogen of 25 standard l/h, maintained at 280° C. for 12 hours and the reactor was finally cooled under a stream of nitrogen.

The pressure was then increased to 180 bar and an amount of 300 ml of DMAPA together with a stream of hydrogen of 50 standard l/h were passed over the catalyst from the bottom upward at 50° C. over a period of 4 h in a single pass.

The hydrogenation of DMAPN was subsequently started. For this purpose, 26.4 g/h of DMAPN, 21.7 g/h of liquid ammonia and 50 standard l/h of hydrogen were passed over the catalyst from the bottom upward. The initial temperature in all experiments was 120° C. Heating was carried out by means of a thermostated oil bath, and the temperature was measured in the oil bath of the jacket. The reactor was operated isothermally.

After passage through the reactor, the reaction mixture was separated into gaseous and liquid components at 180 bar and room temperature. A stream of 80 g/h of the liquid components was recirculated by means of a circulation pump to the inlet of the reactor. Gaseous components were not recirculated. The remaining part of the reaction mixture was depressurized to 20 bar and analyzed by means of an on-line gas chromatograph and finally collected at 1 bar in a receiver.

GC column: 60 m CP Volamine/WCOT Fused Silica 0.32 mm

Temperature program: 50° C.-10 min-15° C./min-240° C.-30 min The DMAPN values reported are in % by weight.

During the first seven days, i.e. the first 168 h, the feed rate of DMAPN was increased stepwise to 52.8 g/h and the $NH_3$ feed rate was increased in parallel to 43.4 g/h in the experiments. After this period of time, the space velocity over the catalyst was thus 2.0 kg of DMAPN per kg of catalyst per hour.

In the experiments, the initial temperature of 120° C. was increased with increasing time of operation in order to compensate for the decrease in conversion caused by deactivation of the catalyst. As soon as the amount of DMAPN determined by gas chromatography exceeded a value of about 0.3%, the temperature in the oil jacket was increased by 2° C. The experiments were operated over a running time of at least 1500 h.

The deactivation of the catalyst was quantified as follows:
Ratio of: temperature increase required (over the running time starting from a jacket temperature of 120° C. in order to ensure a residual DMAPN content of ≤0.3%) to running time.

This indicates the average number of hours after which the temperature has to be increased by 1° C.

Example 1

The DMAPN having a content of 2-(dimethylaminomethyl)glutaronitrile (DGN) of 227 ppm from Example a) was used.

After a period of operation of 1600 h, a temperature of 120° C. was still sufficient to keep the residual DMAPN content below 0.3%. The deactivation of the catalyst was thus less than 1° C./1000 h (120° C.-120° C./1600 h<1° C./1000 h).

Example 2

Comparative Example

The DMAPN having a content of 2-(dimethylaminomethyl)glutaronitrile (DGN) of 373 ppm from Example b) was used.

After 1700 h, a temperature of 128° C. had to be set to keep the residual DMAPN content at about 0.3%.

The deactivation of the catalyst was thus 1° C./213 h (128° C.-120° C./1700 h=8° C./1700 h).

Example 3

The DMAPN having a content of 2-(dimethylaminomethyl)glutaronitrile (DGN) of 27 ppm from Example c) was used.

After a period of operation of 1600 h, a temperature of 120° C. was sufficient to keep the residual DMAPN content significantly below 0.3%.

The deactivation of the catalyst was thus significantly below 1° C./1000 h (120° C.-120° C./1700 h<1° C./1000 h).

Comparison of Examples 1-3 shows that the rate of deactivation of the catalyst is lowest in Examples 1 and 3 and highest in Example 2.

Example 4

Preparation of DMAPN Having a DGN Content of <<300 ppm by Distillation

DMAPN having the following composition (in respect of organic components) is placed in a laboratory distillation apparatus having a Vigreux column (GC analysis: column: 30 m RTX-5; ID=0.32 mm, film thickness=1.5 μm; temperature program: 70° C.-7° C./min-280° C.-30 min; valuation in percent by area):
96.97% of DMAPN
2.95% of dimethylamine
0.02% of 2-(dimethylaminomethyl)glutaronitrile (200 ppm)
The water content was 0.3%.

A small proportion of distillate comprising predominantly DMAPN was then taken off by distillation at 100 mbar and temperatures at the bottom and top of not more than 100° C.

The composition of the remaining bottoms was:
>99.90% of DMAPN
<0.01% of dimethylamine
0.02% of 2-(dimethylaminomethyl)glutaronitrile
The water content was 0.02%.

In a second step, the bottom product was distilled at 100 mbar and a temperature at the bottom and top of at least 100° C. until only a small amount of residue remained in the distillation flask. The distillate was found to have the following composition:
99.95% of DMAPN
2-(Dimethylaminomethyl)glutaronitrile was not detected.
A DGN-free DMAPN could thus be obtained.

Example 5

Preparation of DMAPN by a Method Based on Example 2 of WO-2007/128803 (Comparative Example)

The addition of DMA onto ACN was carried out in a continuously operated cascade comprising seven stirred vessels. The volume ratio of the seven stirred vessels was 1:1.5:2.5:3.4:3.4:3.4:3.4. The reaction was carried out at a pressure of 5 bar.

The temperature in the first two stirred vessels was 60° C., and that in the third to seventh vessels was 40° C. The addition reaction was carried out at a space velocity calculated as inflow of acrylonitrile per unit time based on the volume of the first stirred vessel of 0.54 kg/l/h. The molar ratio of DMA to ACN introduced was 0.98. The residual acrylonitrile content was about 2% by weight (based on the total output from the reaction). The average residence time of the reaction mixture in the vessels of the addition reaction stage was about 16 hours.

An amount of 1406 g of the DMAPN prepared in this way was distilled to a residue of 10 g as described above (see Example a)). A GC analysis was carried out on this residue (cf. Example a)):

DGN was detected at a retention time of 16 min.

The content of DGN, based on the amount of DMAPN originally used in the distillation (1406 g), was 427 ppm.

The invention claimed is:

1. A process for preparing 3-dimethylaminopropylamine (DMAPA) by reacting 3-dimethylaminopropionitrile (DMAPN) with hydrogen in the presence of a catalyst, wherein the DMAPN used applied in form of 2-(dimethylaminomethyl)glutaronitrile (DGN) free DMAPN or a mixture comprising DMAPN and DGN with a content of DGN of 300 ppm by weight or less, based on the DMAPN used.

2. The process according to claim 1, wherein the mixture of DMAPN and DGN has a content of DGN of 100 ppm by weight or less, based on the DMAPN used.

3. The process according to claim 1, wherein the preparation of the mixture comprising DMAPN and DGN with a content of DGN of 300 ppm or less is carried out by continuously reacting acrylonitrile with dimethylamine to give a mixture comprising DMAPN and DGN and working up the mixture comprising DMAPN and DGN by distillation.

4. The process according to claim 3, wherein the distillation is carried out in a column arrangement comprising a column for separating off low boilers and a further distillation column for separating off the relatively nonvolatile secondary components.

5. The process according to claim 3, wherein the distillation is carried out in a column in which low boilers are obtained at the top, high boilers are obtained at the bottom and DMAPN is obtained via a gaseous side offtake stream.

6. The process according to claim 3, wherein the distillation is carried out in a column which has a dividing wall in the middle part and in which the low boilers are obtained at the top, high boilers are obtained at the bottom and DMAPN is obtained on the side of the dividing wall opposite the feed point.

7. The process according to claim 2, wherein the distillation is carried out in a column arrangement comprising a column for separating off low boilers and a further distillation column for separating off the relatively nonvolatile secondary components.

8. The process according to claim 2, wherein the distillation is carried out in a column in which low boilers are obtained at the top, high boilers are obtained at the bottom and DMAPN is obtained via a gaseous side offtake stream.

9. The process according to claim 2, wherein the distillation is carried out in a column which has a dividing wall in the middle part and in which the low boilers are obtained at the top, high boilers are obtained at the bottom and DMAPN is obtained on the side of the dividing wall opposite the feed point.

10. The process according to claim 1, wherein dimethylaminopropionitrile (DMAPN) is prepared by reacting dimethylamine and acrylonitrile in the presence of water in a reactor cascade in a temperature range from 50 to 80° C. and a pressure range from 3 to 8 bar, where the molar ratio of DMA to ACN is in the range from 1.02:1 to 1.10:1 and the proportion of water is in the range from 1 to 8% by weight, based on the sum of the DMA and ACN used.

11. The process according to claim 2, wherein dimethylaminopropionitrile (DMAPN) is prepared by reacting dimethylamine and acrylonitrile in the presence of water in a reactor cascade in a temperature range from 50 to 80° C. and a pressure range from 3 to 8 bar, where the molar ratio of DMA to ACN is in the range from 1.02:1 to 1.10:1 and the proportion of water is in the range from 1 to 8% by weight, based on the sum of the DMA and ACN used.

12. The process according to claim 1, wherein the catalyst comprises Co or Ni as active species.

13. The process according to claim 12, wherein the catalyst is produced by reduction of an oxygen compound of Co.

14. The process according to claim 11, wherein the catalyst comprises Co or Ni as active species.

15. The process according to claim 14, wherein the catalyst is produced by reduction of an oxygen compound of Co.

16. A process for preparing 3-dimethylaminopropylamine (DMAPA) which comprises reacting a mixture of 3-dimethylaminopropionitrile (DMAPN) which contains 2-(dimethylaminomethyl)glutaronitrile (DGN) in an amount of 300 ppm by weight or less based on the DMAPN used with hydrogen in the presence of a catalyst.

17. The process according to claim 1, wherein the preparation of the mixture comprising DMAPN and DGN with an amount of 300 ppm or less is carried out by
a) continuously reacting acrylonitrile with dimethylamine to give a mixture comprising DMAPN and DGN and working up the DMAPN-comprising reaction mixture by distillation or
b) reacting dimethylamine and acrylonitrile in the presence of water in a reactor cascade in a temperature range from 50 to 80° C. and a pressure range from 3 to 8 bar, where the molar ratio of DMA to ACN is in the range from 1.02:1 to 1.10:1 and the proportion of water is in the range from 1 to 8% by weight, based on the sum of the DMA and ACN used.

18. The process according to claim 1, wherein the DMAPN has a DGN content of at least 5 ppm.

* * * * *